United States Patent [19]
Marsolier et al.

[11] Patent Number: 5,905,025
[45] Date of Patent: May 18, 1999

[54] CHIMERIC PROTEINS ACTIVATING POLYMERASE III TRANSCRIPTION, USE THEREOF FOR DETECTING AND ANALYSING PROTEIN-PROTEIN INTERACTIONS AND GENES CODING FOR SAID PROTEINS

[75] Inventors: Marie-Claude Marsolier, Paris; André Sentenac, Bures-Sur-Yvette, both of France

[73] Assignee: Commissariat a l'Energie Atomique-C.E.A., Paris Cedex, France

[21] Appl. No.: 08/952,504

[22] PCT Filed: May 24, 1996

[86] PCT No.: PCT/FR96/00780

§ 371 Date: Nov. 26, 1997

§ 102(e) Date: Nov. 26, 1997

[87] PCT Pub. No.: WO96/37618

PCT Pub. Date: Nov. 28, 1996

[30]  Foreign Application Priority Data

May 26, 1995 [FR] France .................................. 95 06249

[51] Int. Cl.$^6$ .......................... C07K 14/00; C12N 15/62; C12Q 1/68
[52] U.S. Cl. ................................ 435/6; 530/350; 536/23.4
[58] Field of Search .................................. 435/6, 7.1, 7.2, 435/7.31; 530/350; 536/23.4

[56]  References Cited

PUBLICATIONS

Marsolier,M–C et al : "The antirepression role of general class III transcription factors," Journal of Cellular Biochemistry Supplement 0 (21B); 1995; 150. Abstract No. J8–001.

B. Le Douarin et al, "A new version of the two–hybrid assay for detection of protein–protein interactions," Nucleic Acids Research, vol. 23, No. 5, Mar. 11, 1995, pp. 876–878.

Marsolier, M–C et al, "Directing transcription of an RNA polyerase III gene via GAL4 sites," Proceedings of the National Academy of Sciences of the U.S., 91 (25). 1994. 11938–11942.

P. Legrain and C. Chapon, "Interaction betweenn PRP11 and SPP91 yeast splicing factors and characterization of a PRP9–PRP11–SPP91 complex", Science, vol. 262, Oct. 1, 1993, AAAS, Wash. D. C., pp. 108–110.

M. Werner et al, "Interaction between a complex of RNA polymerase III subunits and the 70–kDa component of transcription factor IIIB", J. Biol. che., vol. 268, No. 28, Oct. 5, 1993, Am. Soc. Biochem. Mol. Biol., Inc., Baltimore, US., pp. 20721–20724.

J.E.Arenas and J.N. Abelson, "The *Saccharomyces cerevisiae* PRP21 gene product is an integral component of the spliceosome," Proc. Natl. Acad Sci., vol. 90, Jul. 1990, Natl. Acad Sci., Wash. D.C., pp. 6771–6775.

M–C Marsolier et al, "reciprocal interferences between nucleosomal organization and transcriptional activity of the yeast SNR6 gene," Genes & Development, vol. 9, No. 4, Feb. 15, 1995, pp. 410–422.

*Primary Examiner*—Nancy Degen
*Assistant Examiner*—Robert Schwartzman
*Attorney, Agent, or Firm*—Oblon, Spivak, McClelland, Maier & Neustadt, P.C.

[57]  ABSTRACT

Genes coding for chimeric proteins activating polymerase III transcription, the chimeric proteins and the use thereof for detecting and analysing protein-protein interactions are described. The chimeric proteins are obtained by fusing a polypeptide which is a polymerase PolIII transcription promoter with a polypeptide which is a first member of a protein-protein interaction pair.

7 Claims, 7 Drawing Sheets

CHIMERIC PROTEINS ACTIVATING POLYMERASE III TRANSCRIPTION, USE THEREOF FOR DETECTING AND ANALYSING PROTEIN-PROTEIN INTERACTIONS AND GENES CODING FOR SAID PROTEINS

This application is a 371 of PCT/FR96/00780.

BACKGROUND OF THE INVENTION

1. Field of the Invention

The present invention relates to new means for detecting and analysing the interactions between proteins

2. Discussion of the Related Art

Protein/protein interactions are fundamental cellular mechanisms which are involved in the formation of multimeric complexes responsible both for functions such as transcription and translation, and for the transmission of signals, the response to pathogenic agents and the like.

To analyse these interactions, conventional biochemical techniques (cross-linking, co-immunoprecipitation, co-fractionation by chromatography) which are intended to isolate the proteins interacting with a target protein are generally difficult to use, especially when the interacting proteins are in a small quantity. In addition, they make it possible to identify the interacting proteins, but not to directly obtain the genes corresponding to the said proteins.

One procedure called: "double-hybrid method", which makes it possible to detect interactions between 2 proteins, has been developed by FIELDS and SONG [FIELDS and SONG, Nature, 340, 245–246 (1989) and Patent U.S. Pat. No. 5,283,173].

This procedure is based on the co-expression, in the same yeast cell, of the following genes:

one reporter gene expressing a detectable protein, whose level of expression depends on transcriptional activation by a polypeptide domain; and two chimeric genes, encoding two hybrid proteins comprising respectively the sequences of the two proteins whose interaction it is desired to detect: one comprises, in addition, a transcription activation domain regulating the expression of the reporter gene, the other comprises, in addition, a DNA-binding domain, which recognizes a binding site situated on the reporter gene in the host cell.

When the two chimeric genes are expressed in the same cell, if an interaction occurs between the two proteins, it causes the transcription activation domain and the reporter gene to come into contact due to the attachment of the DNA-binding domain to its site situated on the reporter gene. The transcription of the latter is activated, and an increase in its expression product can therefore be observed.

In the system described in Patent U.S. Pat. No. 5,283,173, FIELDS and SONG exploited more particularly the properties of GAL4, a transcription activator in *Saccharomyces cerevisiae*.

GAL4 activates the transcription by RNA polymerase II (PolII) of genes encoding enzymes involved in the metabolism of galactose. This protein comprises 2 functionally independent and physically separable domains: one DNA-binding domain, represented by the N-terminal domain (amino acids 1–147) which binds to specific sequences of the DNA (UAS$_G$, for Upstream Activating Sequence for Galactose), and a transcription activation domain represented by the C-terminal domain (amino acids 768–881), which activates the transcription by PolII.

Two types of hybrid proteins can thus be produced from GAL4: one contains the GAL4(1–147) domain fused to a first test protein, the other contains the GAL4(768–881) domain fused to a second test protein. If the 2 test proteins are capable of interacting, they bring the two domains of GAL4 closer and trigger the transcription of the reporter gene (for example the lacZ gene encoding the β-galactosidase of *E. coli*).

It is possible to simultaneously test several proteins with the aim of investigating their interactions with a given protein. For example, the protein whose partners are sought is fused with the binding domain GAL4(1–147) and it is tested against a library of proteins fused with the activator domain GAL4(768–881).

Numerous improvements have been made to the technique initially used by FIELDS and SONG: for example a system for cloning into λ phages subsequently convertible to plasmids by recombination of lox sites, has been developed; a second reporter gene, consisting of a marker for auxotrophy, the HIS3 gene (involved in the metabolism of histidine), was used in combination with the lacZ gene in order to eliminate the false positives more efficiently [DURFEE et al., Genes & Development, 7, 555–569, (1993)].

Variants of this technique have also been proposed: thus the non-exclusive aspect of 2 interactions of a protein A with 2 other proteins B and C can be demonstrated by the difference in transcription activation between a system comprising only the 2 hybrids B and C fused with GAL4-(1–147) and GAL4-(758–881) respectively, and a system comprising the 2 hybrids B and C as well as the protein A non-fused but simply overexpressed, and which forms an intermediate between B and C [LEGRAIN and CHAPON, SCIENCE, 262, 108–110, (1993)].

A derived technique, called single-hybrid system, makes it possible to detect proteins attaching to DNA fragments (for example promoters or fragments involved in the replication of the DNA). In this case, only the hybrid proteins encoded by a library of cDNAs fused with GAL4-(768–881) are used. This library is introduced into cells containing a reporter gene (HIS3 or lacZ) placed downstream of the DNA fragment studied [WANG and REED, NATURE, 364, 121–126, (1993); LI and HERSKOWITZ, SCIENCE, 262, 1870–1874, (1993)].

Related strategies have also been developed for identifying the DNA sequences to which a given protein binds [WILSON et al., SCIENCE, 252, 1296–1300, (1991)], or for selecting functional mutations in protein domains which bind to DNA [WILSON et al., Proc. Natl. Acad. Sci. USA, 90, 9186–9190, (1993)].

The major limitation of this system is linked to the fact that the protein whose partners are being sought should not exhibit PolII transcription activating activity. This limit therefore excludes the study, by this technique, of the physiological PolII activators (involved in pathological or normal PolII transcription regulation mechanisms), and, in general, of the proteins which, fortuitously, possess activating properties. Now, such properties are not rare: PolII transcription activation by proteins which are not physiological PolII activators has been reported; it has also been shown that 1% of the *E. coli* genomic fragments randomly generated by digestion with Sau3A, when they are fused with the domain encoding GAL4(1–147), encode peptides which activate the PolII transcription [MA and PTASHNE, Cell., 51, 113–119, (1987)].

The inventors have undertaken the development of a system which does not possess this limitation. For this purpose, they had the idea of searching for a method based on the use of the PolIII system.

However, to achieve a double-hybrid system based on the use of polymerase III, it was necessary, on the one hand, to identify transcription factors for the PolIII system capable of being used for this purpose, and, on the other hand, to have an appropriate reporter gene.

The PolIII system transcribes "housekeeping" genes, whose products (tRNA, 5S rRNA, U6 RNA and the like) are necessary for the basic functions (translation, splicing and the like) of any active cell. The functioning of the PolIII system requires the presence of various transcription factors which ensure correct positioning of polymerase III. For example, the transcription of the tRNA genes involves, first of all, a factor called TFIIIC or τ which binds to intragene sequences called A block and B block. The attachment of τ onto the B block involves the subunit τ138 and its attachment to the A block, the subunit τ95. Once attached, τ then allows the recruitment of another factor, called TFIIIB, within the vicinity of the site of initiation of transcription. For its part, TFIIIB allows the recruitment and positioning of polymerase III on the gene.

In the case of the gene for U6 RNA (called SNR6), the PolIII promoter comprises an intragene A block, a B block downstream of the signal for termination of transcription of the gene, and a TATA box at position −30. A succession of steps analogous to that described for the tRNA genes makes it possible to initiate the transcription of SNR6. These steps are schematically represented in FIG. 1. The τ138 subunit of the τ factor first binds to the B block (1), then the τ95 subunit to the A block (2). The attachment of τ makes it possible to recruit TFIIIB via the τ131 subunit (3). The precise role of the other subunits (τ50, τ60 and τ91) has not yet been established. TFIIIB, which is composed of subunits of 70 kD (70), 90 kD (90) and of TBP (TATA-binding protein, a protein attaching to the TATA box) is positioned upstream of SNR6 (4) and then allows the recruitment of the polymerase PolIII (5). The binding of τ138 onto the B block of SNR6 therefore constitutes one of the first stages of the transcriptional activation of this gene. A mutation of the B block (deletion of bases +238 and +239 relative to the site of initiation of transcription of SNR6) which abolishes this binding prevents the transcription of the SNR6 gene [BROW and GUTHRIE, Gene & Development 4, 1345–1356 (1990); BURNOL et al., Nature, 362, 475–477, (1993)].

During previous studies, the inventors demonstrated that it was possible to re-establish the transcription of the SNR6 gene by inserting, inside the mutated B block of SNR6, $UAS_G$ sequences, and by using a chimeric transcription factor, GAL4-(1–147)-τ138, resulting from the fusion of the binding domain GAL4-(1–147) and τ138 [MARSOLIER et al., Proc. Natl. Acad. Sci. USA, 91, 11938–11942, (1994)]. This transcription mechanism is schematically represented in FIG. 2. These experiments were carried out in the presence of a wild-type SNR6 gene, in order to produce transcripts in a quantity sufficient to ensure cell viability.

SUMMARY OF THE INVENTION

Chimeric proteins, comprising: the fusion of a subunit of polymerase III transcription factor TFIIIB or TFIIIC with a polypeptide constituting one member of a protein/protein interacting pair other than GAL4-(1–147); genes encoding such chimeric proteins, and processes for detecting the interactions between two proteins by detecting expression of a reporter gene transcribed by the PolIII polymerase in a host cell.

Figure 1:
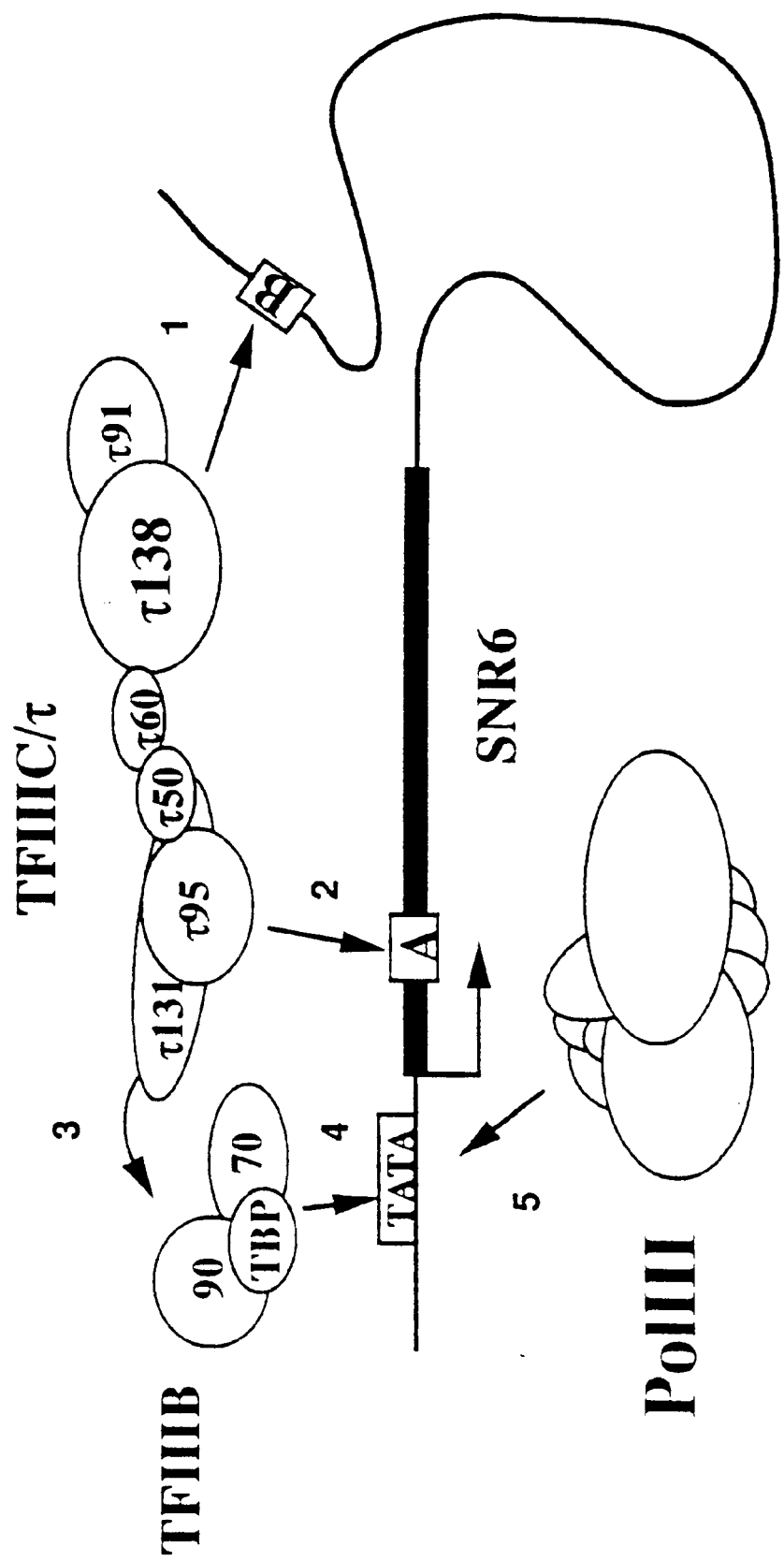
FIG. 1 schematically shows the factors needed to initiate transcription of SNR6.
Figure 2:
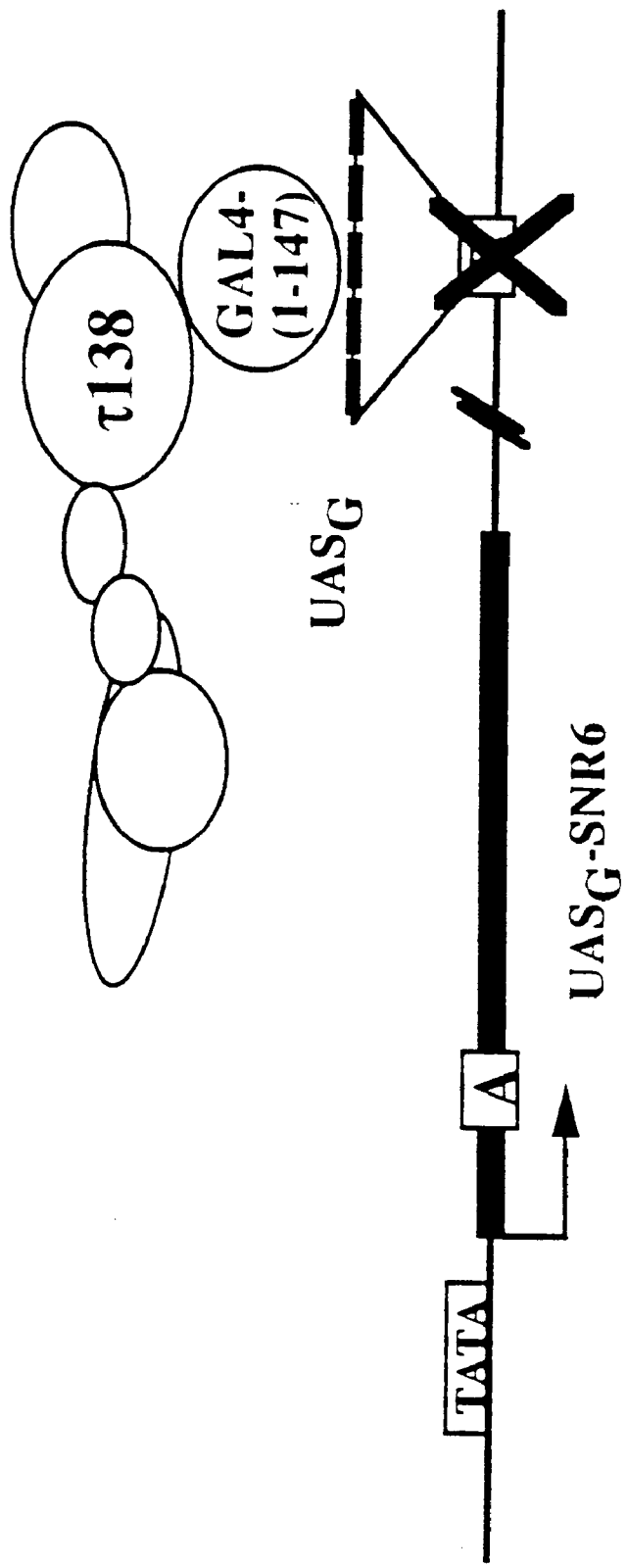
FIG. 2 shows the transcription of the SNR6 gene containing a mutated B block, $UAS_G$ sequences, and a chimeric transcription factor GAL4-(1–147)-τ138.

The inventors have now observed that the transcription of the mutated SNR6 gene via the fusion protein GAL4-(1–147)-τ138 could provide enough transcripts to allow the cells to grow without the presence of the wild-type SNR6 gene.

Indeed, the inventors introduced plasmids comprising the SNR6 gene without the B block and with $UAS_G$ sequences, as well as plasmids comprising the construct GAL4-(1–147)-τ138, into the yeast strain yMCM616.

In the disclosure of the present invention, the expression "without the B block", should be understood to mean "without a functional B block" capable of recognizing τ138.

yMCM616 is a derivative of the YPH500α strain, [SIKORSKI and HIETER, Genetics, 122, 19–27, (1989)], whose chromosomal SNR6 gene has been mutated, and which survives with a wild-type SNR6 gene carried by a plasmid URA3. This strain does not grow in the presence of 5-fluoroorotic acid, which is metabolized into a toxic compound by the product of the URA3 gene [BOEKE et al., Molecular and General Genetics, 197, 345 (1984)].

Likewise, the yMCM616 transformants comprising the construct GAL4-(1–147)-τ138 alone, or alternatively the construct GAL4-(1–147)-τ138 and SNR6 genes without the B block and without $UAS_G$ sequences do not grow in the presence of 5-fluoroorotic acid (5-FOA).

Now, the inventors have observed that, on the other hand, the yMCM616 transformants, comprising the construct GAL4-(1–147)-τ138 and the SNR6 gene without the B block and with $UAS_G$ sequences are capable of growing in the presence of 5-fluoroorotic acid, that is to say of losing the plasmid URA3 carrying the wild-type SNR6 gene, which shows that the presence of the wild-type SNR6 gene is not necessary for the cellular viability of these transformants.

The inventors had the idea of investigating if this process of activation of PolIII via GAL4-(1–147)-τ138 could allow the detection of protein/protein interactions.

For this purpose, two pairs of yeast nuclear proteins (cleavage factors PRP), whose interactions were previously demonstrated in the PolII double-hybrid system [LEGRAIN et al., Genes & Development, 7, 1390–1399, (1993) and LEGRAIN and CHAPON, Science, 262, 108–110, (1993)], namely the pairs PRP9/PRP21 and PRP11/PRP21, were used.

Plasmids respectively called GAL4-(1–147)-PRP9, and GAL4-(1–147)-PRP11, and comprising the entire sequences encoding PRP9 or PRP11, fused with the sequence encoding the 147 N-terminal amino acids of GAL4, have been constructed. Likewise, a plasmid (τ138-PRP21) has been constructed, which comprises the entire sequence encoding τ138 fused with the coding region of PRP21.

These various plasmids were introduced into the yMCM616 strain at the same time as the plasmid comprising the SNR6 gene lacking the B block, with or without $UAS_G$ sequence.

The inventors also observed that the presence of the three types of plasmids (namely a plasmid carrying the construct τ138-PRP21, a plasmid carrying the construct GAL4-(1–147)-PRP9 or GAL4-(1–147)-PRP11, and a plasmid carrying the SNR6 gene without the B block and with $UAS_G$ sequences) is necessary to allow the transformants to grow in the presence of 5-fluoroorotic acid. On the other hand, no cell growth is observed when one of the plasmids GAL4-(1–147)-PRP9/11 or τ138-PRP21 is missing or when the SNR6 genes lacking the B block also lack $UAS_G$ sequences.

Figure 3:
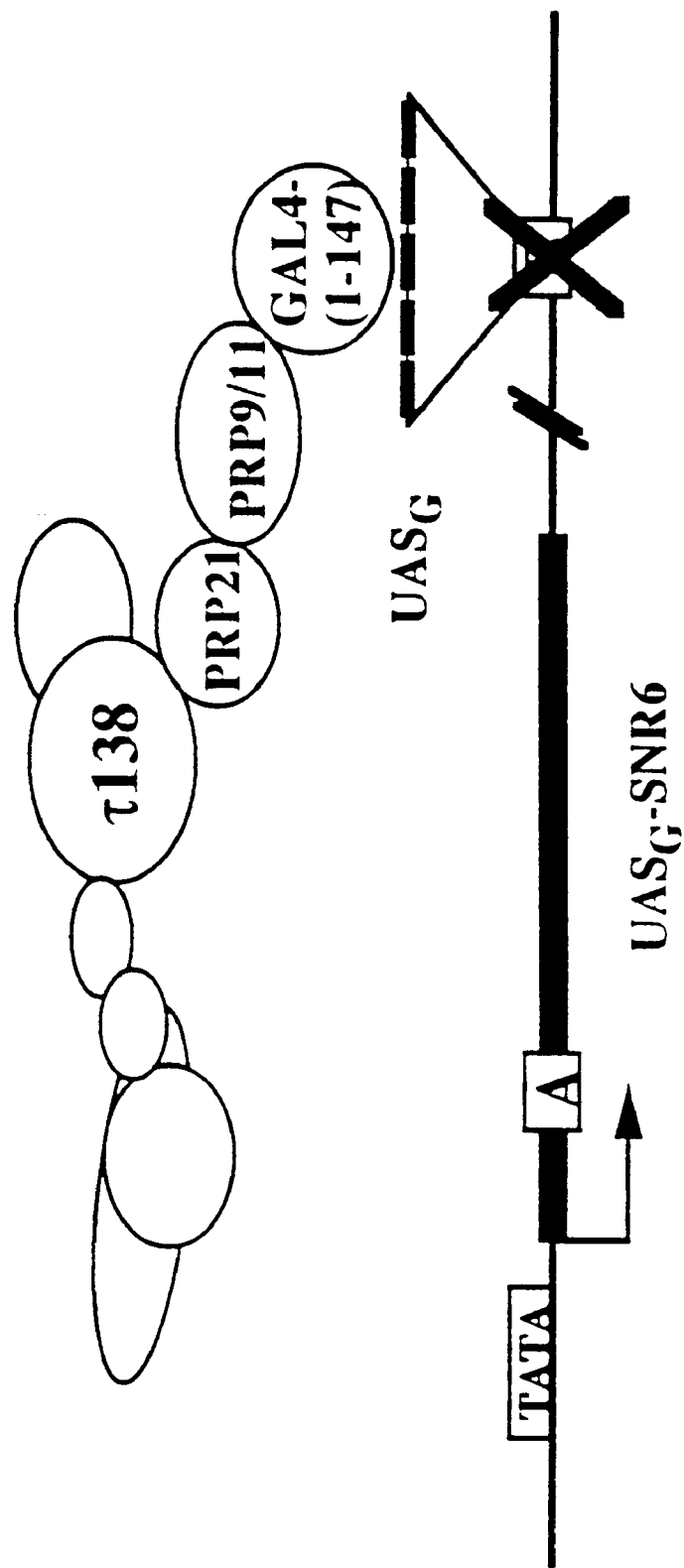
FIG. 3 is a transcription system of the present invention.

The inventors obtained chimeric proteins, one resulting from the fusion of GAL4-(1–147) with a protein which is a member of an interacting pair, and the other resulting from the fusion of τ138 with the other member of the said interacting pair, and they observed that the interaction between these two fusion proteins reproduced the activity of the transcription factor GAL4-(1–147)-τ138. The transcription system thus obtained is schematically represented in FIG. 3.

In addition, the efficiency of transcription by this system makes it possible to obtain enough transcripts to ensure cell viability, and therefore to perform a selection test based on the viability of the cells.

SUMMARY OF THE INVENTION

The subject of the present invention is a chimeric protein resulting from the fusion of a polypeptide constituting a PolIII transcription activator, with a polypeptide constituting a member of a protein/protein interacting pair.

According to a preferred embodiment of the present invention, the polypeptide constituting an activator of transcription by the PolIII polymerase is a subunit of a PolIII transcription factor or a subunit of the PolIII polymerase itself, or represents at least a portion of one of these subunits.

According to a preferred procedure of this embodiment, the polypeptide constituting an activator of transcription by PolIII polymerase is chosen from the group consisting of the subunits of the TFIIIC factor (τ138, τ131 and the like), and the polypeptides representing a portion of the said subunits.

The subject of the present invention is also a gene encoding a chimeric protein as defined above, as well as a recombinant vector carrying the said gene.

The subject of the present invention is also a pair of chimeric proteins comprising a first chimeric protein as defined above, and a second chimeric protein resulting from the fusion of a polypeptide capable of binding to a specific DNA sequence, with a polypeptide constituting the other member of the protein/protein interacting pair mentioned above.

Various polypeptides capable of binding to a specific DNA sequence can be used to construct this second chimeric protein; by way of nonlimiting examples, there may be mentioned: the 1–147 domain of GAL4, which specifically recognizes the $UAS_G$ sequences; the domain of attachment of LexA [BRENT and PTASHNE, Cell, 43, 729–736, (1985)] or that of the human oestrogen receptor [LE DOUARIN et al., Nucleic Acids Research, 23, 876–878, (1995)], and the like.

The subject of the present invention is also a process for detecting the interactions between two proteins, which process is characterized in that the following DNA sequences are introduced into the same host cell:

a DNA sequence (a), at least a portion of which constitutes a reporter gene transcribed by polymerase III; and at least a portion constitutes a binding site recognized by a polypeptide sequence capable of binding to DNA;

a DNA sequence (b), at least a portion of which constitutes a first chimeric gene, comprising a sequence encoding a polypeptide constituting an activator of transcription by the PolIII polymerase, fused with a sequence encoding a polypeptide capable of constituting a member of a protein/protein interacting pair;

a DNA sequence (c), at least a portion of which constitutes a second chimeric gene, comprising a sequence encoding the polypeptide which recognizes the binding site carried by the sequence (a), fused with a sequence encoding a polypeptide capable of constituting the second member of the said protein/protein interacting pair;

in that the said host cell is placed in culture, under conditions allowing the expression of the reporter gene carried by the sequence (a) and in that the expression of the said reporter gene, in the host cell or in its progeny, is detected by any appropriate means.

DETAILED DESCRIPTION OF THE INVENTION

According to a preferred embodiment of the present invention, the reporter gene transcribed by polymerase III is the SNR6 gene.

Other PolIII genes can also be used as reporter genes, as long as their expression brings about the appearance of an observable phenotype. These may be for example genes for tRNA, and in particular, translation termination codon suppressor genes.

This (these) reporter gene(s) may be present in centromeric or multicopy plasmid, or may be integrated into the chromosomes of the host cell.

According to another preferred embodiment of the present invention, the binding site recognized by a polypeptide sequence capable of binding to DNA is a $UAS_G$ sequence, and the polypeptide which recognizes the said binding site is the 1–147 domain of GAL4.

Other polypeptide sequence-binding site combinations can also be used, such as for example the domain of attachment of LexA or that of the human oestrogen receptor, which are mentioned above, these polypeptides are used in combination with their respective DNA target sequences (operators LexA and EREs, oestrogen receptor response elements).

According to another preferred embodiment of the present invention, the polypeptide constituting an activator of transcription by the PolIII polymerase is the subunit τ138 of the factor TFIIIC.

According to yet another preferred embodiment of the present invention, the host cell used is preferably a yeast cell (*Saccharomyces cerevisiae, Schizosaccharomyces pombe* and the like).

The present invention will be understood more clearly with the aid of the additional description which will be given below, which refers to exemplary embodiments of the process in accordance with the invention.

It should be clearly understood, however, that these examples are given solely by way of illustration of the subject of the invention and do not constitute in any manner a limitation thereto.

EXAMPLE 1

Strains and plasmids:

The yMCM616 strain is identical to the FTY115 strain described by MARSOLIER et al., [Genes & Development, 9, 410–422, (1995)], the only exception being that it comprises not the plasmid pRS314-U6, but the centromeric plasmid URA3 pRS316-U6, carrying the region of the SNR6 gene stretching between bases −140 to +314 relative to the site of initiation of transcription. The plasmid pRS316-U6 was obtained from the original plasmid URA3 pRS316, which has been described by SIKORSKI and HIETER, [Genetics, 122, 19–27, (1989)]. The SNR6 region (−140; +314) was cloned between the KpnI and SacI sites of pR316 to give pR316-U6.

Figure 4:
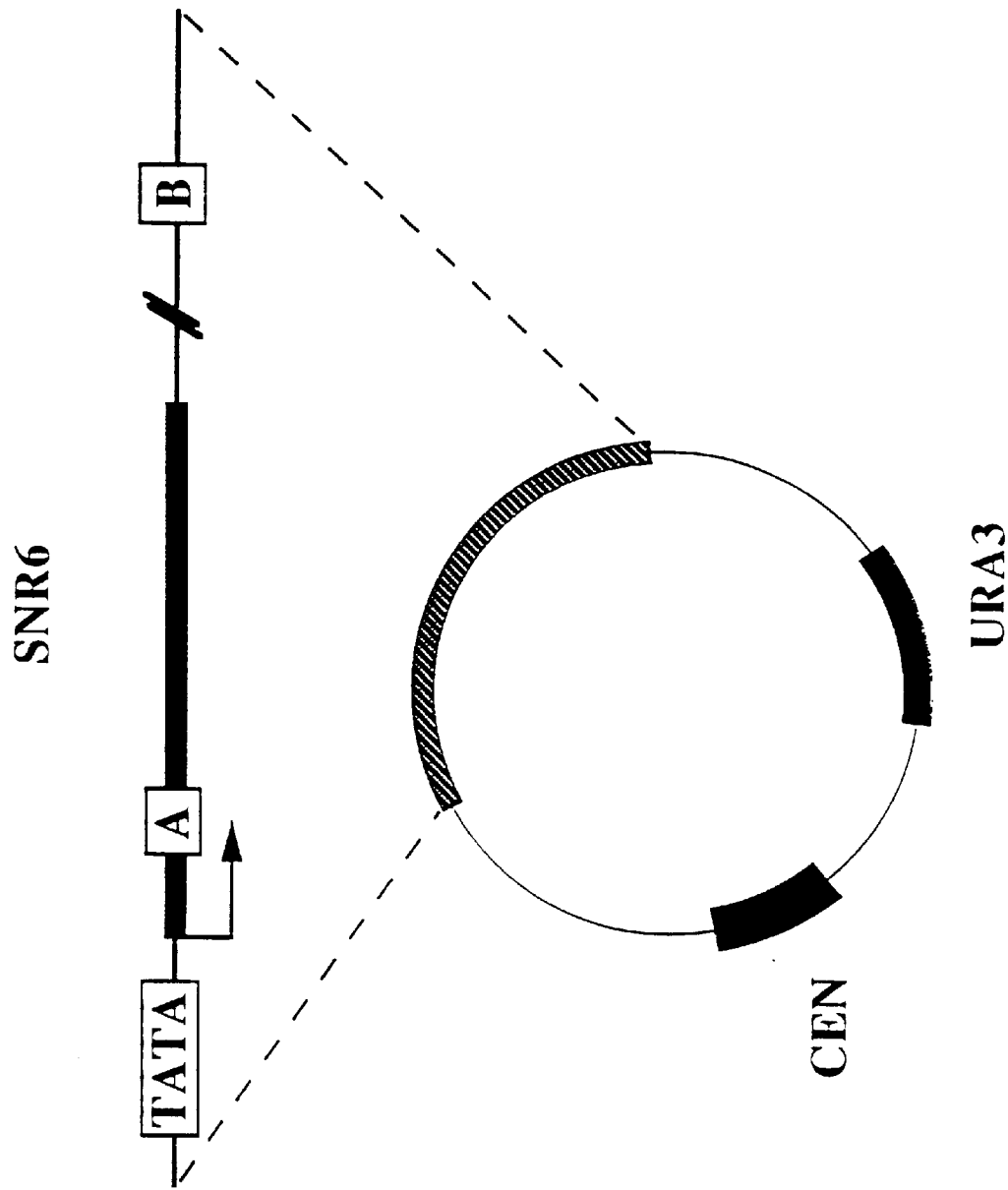
FIG. 4 schematically represents centromeric plasmid URA3 pRS316-U6.

This construct is schematically represented in FIG. 4 (CEN: yeast centromeric sequences; URA3: gene encoding orotidine-5'-phosphate decarboxylase which is involved in the biosynthesis of uracil).

The genotype of the yMCM616 strain is: α, ura3-52, lys2-801$^{amber}$, ade2-101$^{ochre}$, trp1-Δ63, his3-Δ200, leu2-Δ1. Moreover, the wild-type SNR6 chromosomal gene of the initial strain was replaced by a mutant SNR6 gene in which the B block has been inactivated by the deletion of bases 238–239 (from the site of initiation of transcription) [MARSOLIER et al., Genes & Development, vol. 9, 410–422, (1995)].

Figure 5:
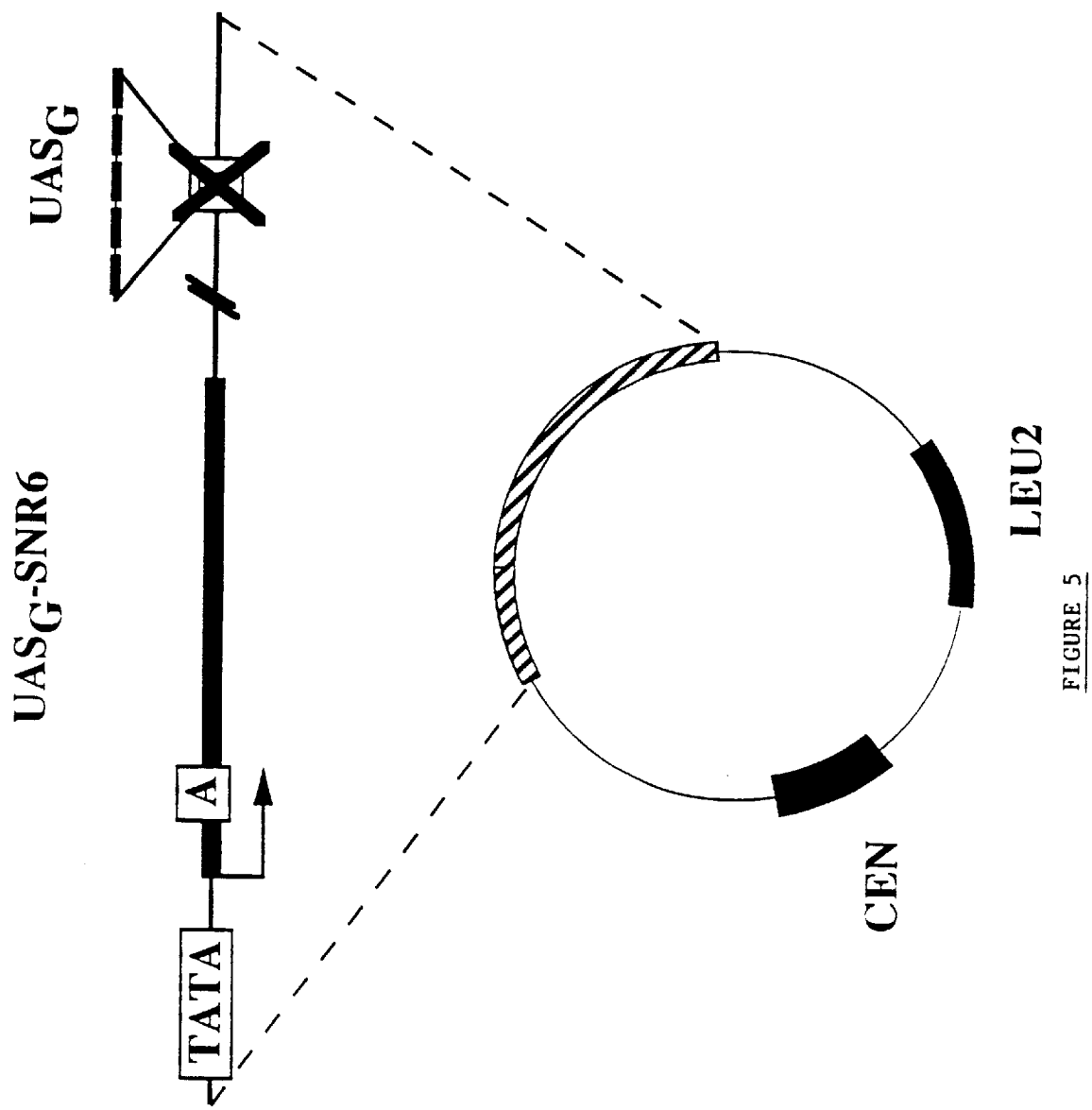
FIG. 5 is a centromeric plasmid encoding β-isopropylmaleate dehydrogenase involved in the synthesis of leucine.

Moreover, an SNR6 gene without the B block and with UAS$_G$ sequences, similar to the construct "B block-UAS$_G$ template" described by MARSOLIER et al., [Proc. Natl. Acad. Sci. USA, 91, 11938–11942, (1994)] apart from the fact that it lacks the 24 bp insert at position +73, was cloned between the ApaI and SacI sites of the centromeric plasmid LEU2, pRS315 [SIKORSKI and HIETER, Genetics, 122, 19–27, (1989)]. This construct is schematically represented in FIG. 5 (CEN: yeast centromeric sequences; LEU2: gene encoding the β-isopropylmalate dehydrogenase involved in the synthesis of leucine).

In addition, the SNR6 gene without the B block and lacking UAS$_G$ sequences of the plasmid pRS314-U6 described by MARSOLIER et al. [Genes & Development, 9, 410–422, (1995)] was recloned between the ApaI and SacI sites of the centromeric plasmid pRS315.

Figure 6:
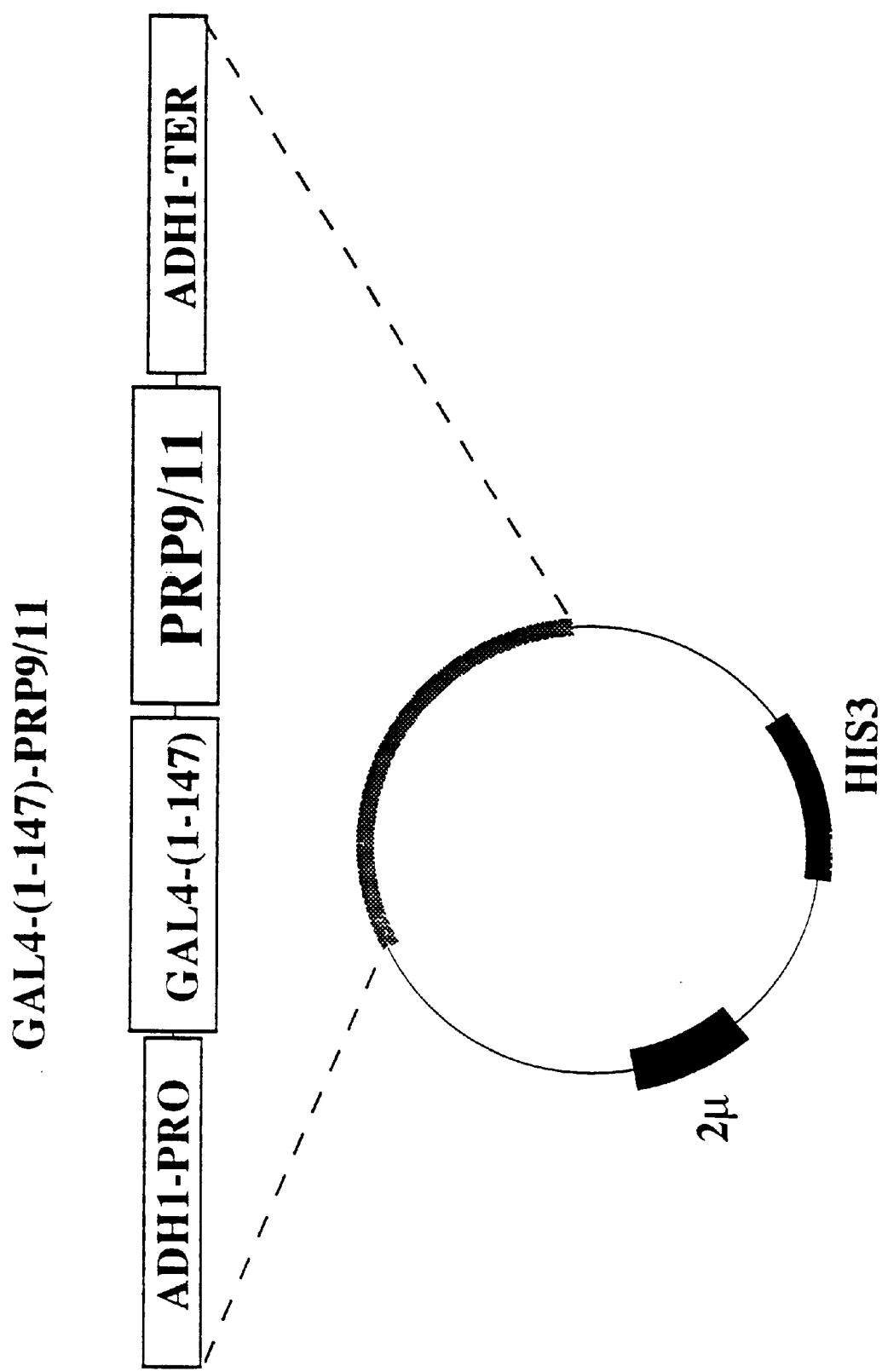
FIG. 6 schematically represent plasmids GAL4-(1–147)-PRP9 and GAL4-(1–147)-PRP11.

Plasmids called GAL4-(1–147)-PRP9, and GAL4-(1–147)-PRP11 respectively, and derived from pMA424 have been previously described [LEGRAIN et al., Genes & Development, 7, 1390–1399, (1993); LEGRAIN and CHAPON, Science, 262, 108–110, (1993)]. These plasmids contain a construct comprising the entire sequence encoding PRP9 or PRP11, fused with the 147 N-terminal amino acids of GAL4. These constructs are schematically represented in FIG. 6 (ADH1-PRO: promoter region for transcription of the yeast ADH1 gene encoding an alcohol dehydrogenase; ADH1-TER: terminator region for transcription of the ADH1 gene; 2 μ: autonomously replicating sequences derived from the 2 μ yeast plasmid; HIS3: gene encoding imidazole-glycerolphosphate dehydrogenase involved in the synthesis of histidine).

Moreover, the construct τ138-PRP21 consisting of the entire sequence of τ138 [LEFEBVRE et al., Proceedings of the National Academy of Science USA, 89, 10512–10514, (1992)] fused with the coding region of PRP21, was obtained as follows:

The τ138 sequence was cloned from the plasmid called pOL101 (provided by Olivier LEFEBVRE, C.E.A-Saclay, Gif-sur-Yvette). pOL101 was obtained as follows: the plasmid pOL45 described by LEFEBVRE et al., [Proceedings of the National Academy of Sciences USA, 89, 10512–10516 (1992)] which contained the τ138 sequence had been modified in order to remove the intron from the gene (LEFEBVRE et al., 1992, already cited). This modified plasmid pOL45 was subsequently mutagenized by site-directed mutagenesis [KUNKEL et al., Methods in Enzymology, 154, 367–382 (1987)]: BamHI sites were introduced, one just before the codon for initiation of τ138, the other just before the termination codons, to give pOL101. The BamHI fragment of pOL101, comprising the entire coding sequence of τ138, was then cloned into the vector pBluescript SK (BSSK, Stratagene) so that the KpnI site of BSSK was located at the 5' end of τ138. The resulting plasmid is called BSSK-τ138.

The PRP21 sequence was cloned from the plasmid called pPL247 (this plasmid was provided by Pierre LEGRAIN, Institut Pasteur, Paris). Briefly, pPL247 was obtained as follows:

A DNA fragment was derived by PCR from the PRP21 gene. This fragment comprises the coding sequence of PRP21 flanked in 5' by a BamHI site introduced in −8 relative to the initiation codon, and in 3' by an EcoRI site, followed by a BamHI site introduced 26 bp after the termination codon. This BamHi-digested DNA fragment was cloned into the BamHi site of pMA424 [LEGRAIN et al., Genes & Development, 7, 1390–1399, (1993)]. The BamHI site in 3' of PRP21 was subsequently eliminated, and the BamHI-PstI fragment of the plasmid containing the PRP21 sequence was cloned into the vector pBluescript SK$^-$ (BSSK, Stratagene), to give pPL247.

The unique BamHI site of pPL247 situated at the 5' end of PRP21, was opened, provided with blunt ends, and relegated so as to be able to subsequently put PRP21 in phase with τ138.

The plasmid pPL247 thus modified was then digested with SpeI and EcoRV, and the resulting fragment, containing PRP21, was inserted between the SpeI and NotI sites provided with blunt ends, of BSSK-τ138. An EcoRI fragment comprising the construct τ138-PRP21 was then introduced into the EcoRI site of the plasmid pYcDE-2. The plasmid pYcDE-2 was provided by B. D. HALL, University of Washington, Seattle, USA. This plasmid is derived from the plasmid pMAC561 [McKNIGHT and McCONAUGHY Proc. Natl. Acad. Sci USA, 80 4412–4416 (1983)] by deletion of an SphI fragment comprising the upstream portion of the promoter of the ADH1 gene, which thus becomes reduced to an EcoRI-SphI fragment, which makes it truly constitutive.

Figure 7:
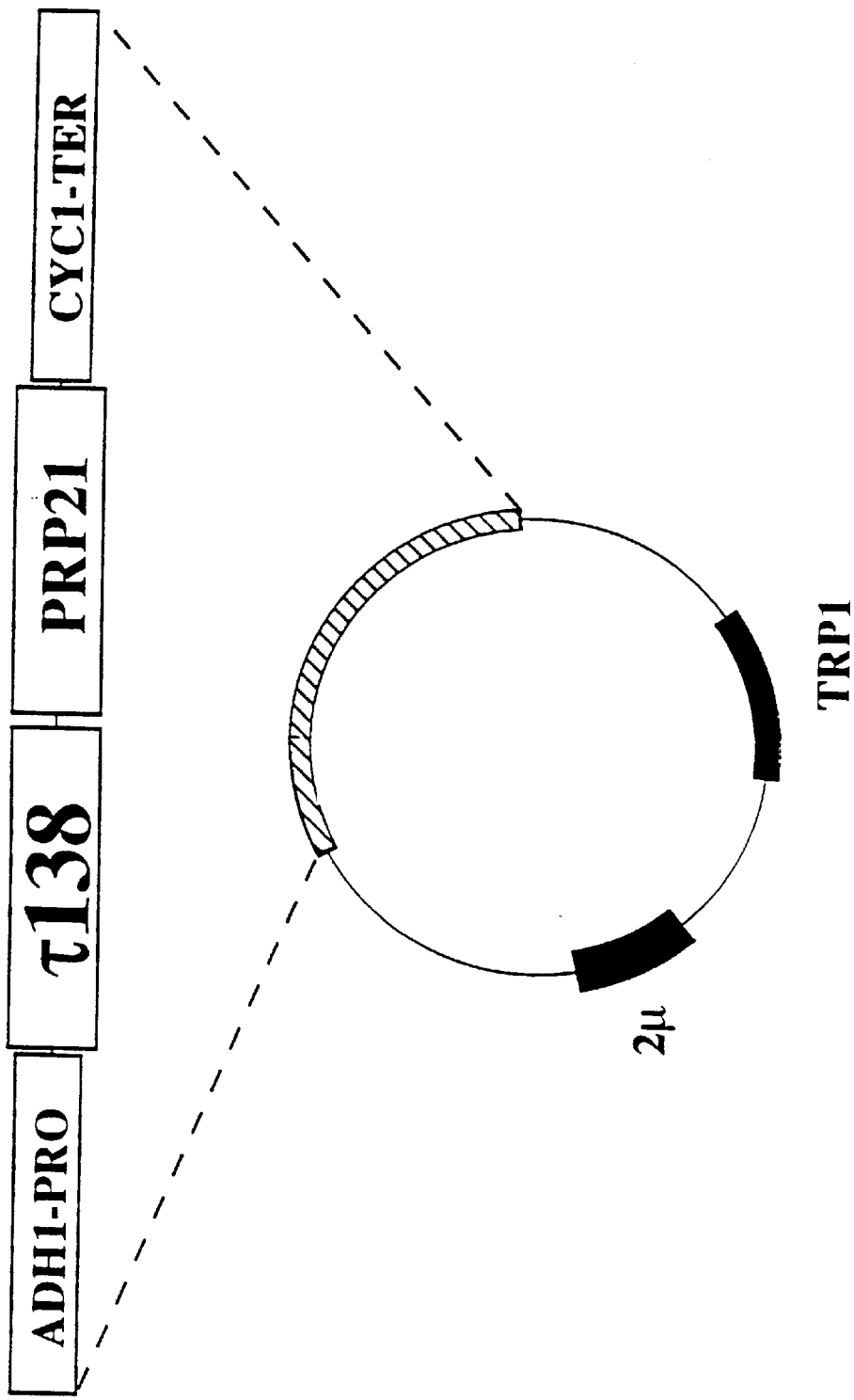
FIG. 7 schematically represent the construction resulting from insertion of chimeric fragment τ138-PRP21 into the EcoRI site of plasmid pYcDE-2.

The construct resulting from the insertion of the chimeric fragment τ138-PRP21 into the EcoRI site of the plasmid pYcDE-2 is schematically represented in FIG. 7 (ADH1-PRO: promoter region for transcription of the yeast ADH1 gene; CYC1-TER: terminator region for transcription of the yeast CYC1 gene encoding iso-1-cytochrome c; 2 μ: autonomously replicating sequences derived from the 2 μ yeast plasmid; TRP1: gene encoding an enzyme involved in the synthesis of tryptophan).

EXAMPLE 2

ACTIVATION OF TRANSCRIPTION BY A POLIII DOUBLE-HYBRID SYSTEM IN ACCORDANCE WITH THE INVENTION

The plasmids containing the constructs:

GAL4-(1–147)-τ138;

τ138-PRP21, and GAL4-(1–147)-PRP9, or GAL4-(1–147)-PRP11;

were introduced into the yMCM616 strain at the same time as the plasmids containing the SNR6 genes lacking the B block, and with or without UAS$_G$ sequence. The transformant clones are selected on minimum media lacking uracil, leucine, histidine or tryptophan (according to the marker genes carried by the plasmids) and are then spread on complete medium in the presence of 5-fluoroorotic acid.

The presence of the three types of plasmids (namely a plasmid carrying τ138-PRP21, a plasmid carrying GAL4-(1–147)-PRP9 or 11, and a plasmid carrying the SNR6 gene lacking the B block and comprising $UAS_G$ sequences) is necessary in order to allow the transformants to grow in the presence of 5-fluoroorotic acid. No cell growth is observed when one of the plasmids GAL4-(1–147)-PRP9/11 or τ138-PRP21 is missing, or when the SNR6 genes lacking the B block also lack $UAS_G$ sequences.

For quantitative analysis of the SNR6 transcripts produced by the double-hybrid system, the transformants containing the constructs GAL4-(1–147)-PRP9/11 and τ138-PRP21 were subcultured several times on 5-FOA medium, and as a result lost the plasmid URA3 containing the wild-type SNR6 gene. Their SNR6 transcripts therefore come exclusively from the transcription of the SNR6 gene without the B block but with the $UAS_G$ sequences via the 2 hybrids.

Several clones were analysed in this manner for each combination of constructs.

The quantity of SNR6 transcripts produced was quantified by RNA transfer, as described previously [MARSOLIER et al., Proc. Natl. Acad. Sci. USA, 91, 11938–11942, (1994)], using the SNR31 gene transcript as internal control. Table I below presents the percentage of SNR6 transcripts produced compared with the yMCM616 strain carrying only the wild-type SNR6 gene on the plasmid pRS316, which represents 100%.

TABLE I

| CONSTRUCTS | QUANTITY OF TRANSCRIPTS (%) |
|---|---|
| GAL4-(1-147)-τ138 | 90% |
| GAL4-(1-147)-PRP9 + τ138-PRP21 | 62% |
| GAL4-(1-147)-PRP11 + τ138-PRP21 | 71% |

These results show that the double-hybrid system in accordance with the invention makes it possible to obtain a high transcription level, representing the production of 60 to 70% of the transcripts produced by the wild-type SNR6 gene possessing an intact B block.

EXAMPLE 3

COMPARISON OF THE POLIII DOUBLE-HYBRID ACTIVATION SYSTEM IN ACCORDANCE WITH THE INVENTION WITH A POLII DOUBLE-HYBRID ACTIVATION SYSTEM

The expression levels obtained with the two activation systems: $UAS_G$-lacZ (PolII double-hybrid) and $UAS_G$-SNR6 (PolIII double-hybrid in accordance with the invention) were compared to those obtained with the "wild-type" activator of each of the two systems.

For $UAS_G$-lacZ, the results presented in Table II below are those reported by MA and PTASHNE, [Cell, 48, 847–853 (1987)] for the wild-type activator and the PolII chimeric activator, and by LEGRAIN at al., [Nucleic Acids Research, 22, 3241–3242, (1994)] for the PolII double-hybrid system; the expression level is determined by measurement of the β-gal activity.

For $UAS_G$-SNR6, the expression level is determined by measurement of the percentage transcription.

The results are presented in Table II below:

TABLE II

| | β-gal activity ($UAS_G$-lacZ) | SNR6 transcripts (%) ($UAS_G$-SNR6) |
|---|---|---|
| Wild-type activator | GAL4-(1-881) | τ138 and wild-type SNR6 gene |
| % expression | 1860 U β-gal = 190% | Transcripts: 110% |
| Chimeric activator | GAL4-(1-147)-GAL4-(768-881) | GAL4-(1-147)-τ138 |
| % expression | 960 U β-gal = 100% | Transcripts: 100% |
| Double-hybrid system | GAL4-(1-147)-PRP9/11 + GAL4-(768-881)-PRP21 | GAL4-(1-147) - PRP9/11 + τ138-PRP21 |
| % expression | 40-60 U β-gal = 4–6% | Transcripts: 69–79% |

These results show that in the case of chimeric molecules where the activating portion of the 2 systems (GAL4-(768–881) for PolII, and τ138 for PolIII, respectively) is fused directly with the binding domain GAL4-(1–147), and where these two domains are therefore strongly attached by covalent bonding, an expression level (which is arbitrarily set at 100%) is obtained which is comparable to a greater or lesser degree with the level obtained with the wild-type genes and activators (190% for PolII with lacZ and 110% for PolIII with SNR6).

On the other hand, when the binding between the activating portion and the DNA-binding domain consists of the interaction between PRP21, and PRP9 or PRP11, the behaviour of the 2 PolII and PolIII systems differs fundamentally. Indeed, with the PolII activation system ($UAS_G$-laCZ), an expression level, measured by a β-gal activity of 40–60 U [LEGRAIN et al., (1994)], is obtained which is relatively small (only 4–6% of the activity obtained with GAL4-(1–147)-GAL4-(768–881)). In contrast, there is obtained for the $UAS_G$-SNR6 gene, and with the same low interaction PRP21-PRP9/11 a transcription level corresponding to 70–80% of that obtained with GAL4-(1–147)-τ138.

We claim:

1. A chimeric protein, comprising: the fusion of a subunit of PolIII transcription factor TFIIIB or TFIIIC with a full length polypeptide constituting one member of a protein/protein interacting pair.

2. The chimeric protein of claim 1, wherein the subunit of TFIIIC is τ138 or τ131.

3. The chimeric protein of claim 1, wherein the subunit of TFIIIB is $TFIIIB_{70}$.

4. DNA encoding a chimeric protein of claim 1.

5. A pair of chimeric proteins, comprising: a first chimeric protein comprising the fusion of a subunit of PolIII transcription factor TFIIIB or TFIIIC, with a polypeptide constituting one member of a protein/protein interacting pair, and a second chimeric protein comprising the fusion of a polypeptide which binds to a specific DNA molecule with a polypeptide constituting the second member of said protein/protein interacting pair.

6. A process for detecting protein/protein interactions, comprising: introducing the following DNA into the same host cell:

a DNA molecule (A), containing a reporter gene which is transcribed by polymerase III and which contains a protein binding site;

a DNA molecule (B), containing a sequence encoding a chimeric protein which is the fusion of a subunit of PolIII transcription factor TFIIIB or TFIIIC with a polypeptide constituting a first member of a protein/protein interacting pair; and a DNA molecule (C), containing a sequence encoding the fusion of a polypeptide which recognizes said protein binding site with a polypeptide which is the second member of said protein/protein interacting pair; then culturing the host cell under conditions which allow expression of said reporter gene and detecting expression of the reporter gene in the host cell or its progeny, wherein detection of reporter gene expression indicates said protein/protein interaction.

7. The process of claim 6, wherein the reporter gene is SNR6, the protein binding site is a $UAS_G$ sequence, and the polypeptide which recognizes the protein binding site is GAL4-(1–147).

* * * * *